United States Patent [19]

Hammann et al.

[11] Patent Number: 5,233,029
[45] Date of Patent: Aug. 3, 1993

[54] ELAIOPHYLIN DERIVATIVES AND A PROCESS FOR THE PREPARATION THEREOF

[75] Inventors: Peter Hammann, Taunus; Gerhard Kretzschmar, Eschborn, both of Fed. Rep. of Germany

[73] Assignee: Hoechst Aktiengesellschaft, Frankfurt am Main, Fed. Rep. of Germany

[21] Appl. No.: 607,285

[22] Filed: Oct. 31, 1990

Related U.S. Application Data

[62] Division of Ser. No. 407,617, Sep. 15, 1989, Pat. No. 4,985,451.

Foreign Application Priority Data

Sep. 17, 1988 [DE] Fed. Rep. of Germany ....... 3831695

[51] Int. Cl.$^5$ .................. C07H 17/08; C07D 409/02; C07D 257/02; C07D 321/00
[52] U.S. Cl. .................... 536/7.1; 536/16.8; 549/267; 548/251; 548/255; 548/263.2; 548/266.2; 548/336; 548/517; 548/305.4; 548/306.1; 548/311.1; 548/313.1
[58] Field of Search .............. 549/267, 60; 548/251, 548/255, 263.2, 266.6, 336, 397, 517; 514/450; 536/7.1, 16.8

[56] References Cited

U.S. PATENT DOCUMENTS 5,011,827  4/1991  Kretzschmar et al. ............. 536/7.1

FOREIGN PATENT DOCUMENTS 0361467  4/1990  European Pat. Off. .

*Primary Examiner*—C. Warren Ivy
*Assistant Examiner*—A. A. Owens
*Attorney, Agent, or Firm*—Finnegan, Henderson, Farabow, Garrett & Dunner

[57] ABSTRACT

The invention relates to elaiophylin derivatives of the formula I, II and III

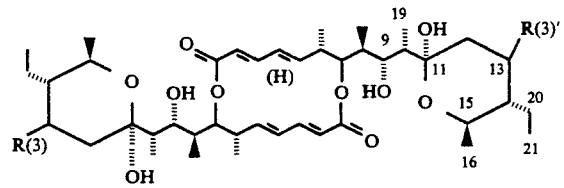

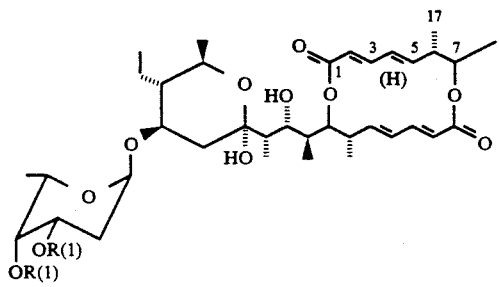

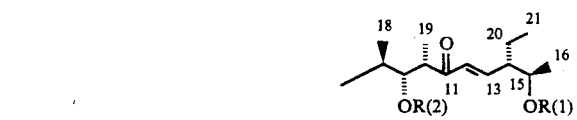

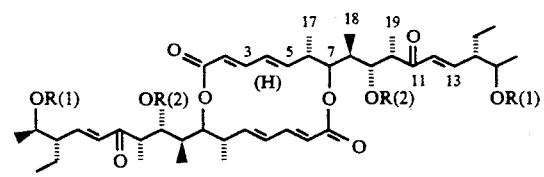

in which the substituents R(1), R(2), R(3) and R(3)' have the specified meanings. The compounds have antibacterial and antiviral activity.

6 Claims, No Drawings

ELAIOPHYLIN DERIVATIVES AND A PROCESS FOR THE PREPARATION THEREOF

S. Takahashi Chem. Pharm. Bull. 15, 1651, 1657, 1726 (1976). The invention now makes available for the first time conditions under which it is possible to eliminate the deoxyfucose from elaiophylin

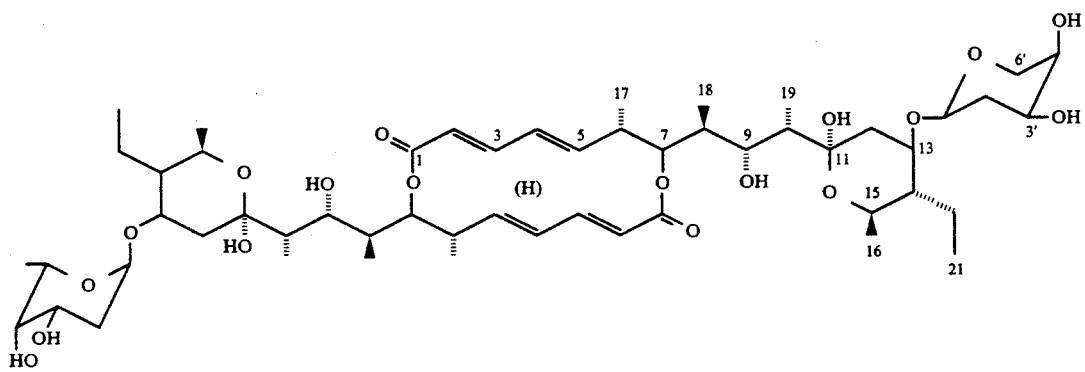

This is a division of application Ser. No. 07/407,617, filed Sep. 15, 1989 now U.S. Pat. No. 4,985,451.

The invention relates to elaiophylin derivatives and to the preparation thereof and the use thereof as pharmaceuticals, in particular as pharmaceuticals having antibacterial and antiviral activity. Elimination of the 2,6-deoxyfucose from elaiophylin gives rise to difficulties because of the instability of the molecule both under acid and under basic conditions, in this connection see D. Seebach, Liebigs Ann. Chem. 1986, page 1281 and W. Keller-Schierlein, Helv. Chim. Acta 64, 407 (1981), by controlled basic reaction conditions to give the unsymmetrical enones II

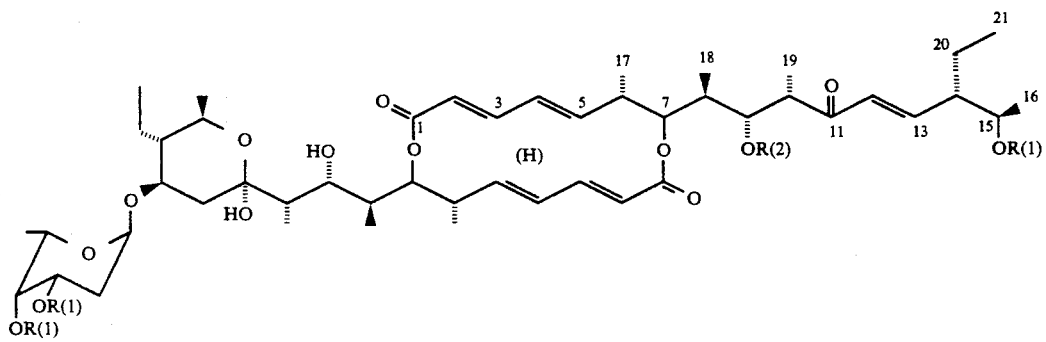

and the symmetrical enones III

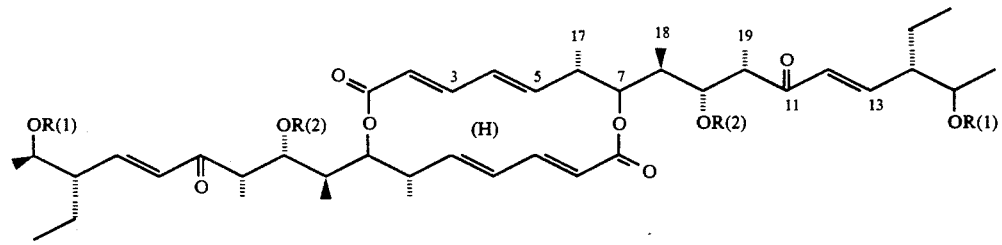

in high yields.

Addition of thio compounds to III results in elaiophylin derivatives I

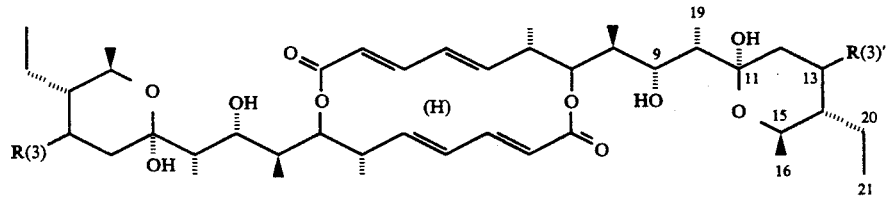

and hydrogenation results in the corresponding octahydro compounds I with R(3)=H and R(3)'=H or R(3)=L-deoxyfucose and R(3)'=H.

Hence the invention relates to compounds I

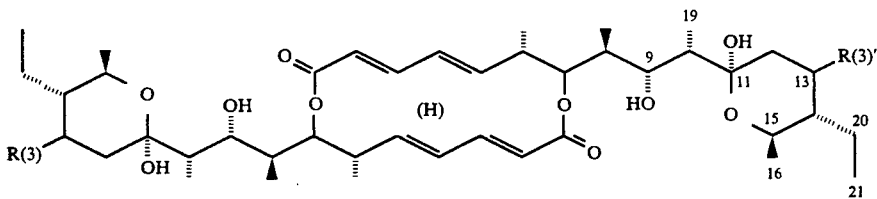

where the C—C double bonds in the macrodiolide ring of the compound of the formula I can also be hydrogenated, the meanings in this formula I being:

a) R(3)′, identical or different, a radical of the formula IV

—SR(4)    IV with R(4) equal to hydrogen, $(C_1-C_{10})$-alkyl which is unsubstituted or substituted by OH or COOH, $(C_2-C_{10})$-alkenyl, $(C_3-C_8)$-cycloalkyl, pyrrolyl, benzopyrrolyl, imidazolyl, benzimidazolyl, triazolyl, tetrazolyl, phenyl, with the aromatic or heteroaryl radicals being unsubstituted or substituted once or twice by $(C_1-C_4)$-alkyl, $(C_1-C_4)$-alkoxy, $(C_1-C_4)$-alkylcarbonyl, carboxyl, F, Cl, Br, I, $NO_2$ or CN.

b) R(3) L-deoxyfucose and R(3)′ as defined under a).

c) If the C—C double bonds in the macrodiolide ring are hydrogenated:
R(3), and R(3)′ hydrogen or R(3) L-deoxyfucose and R(3)′ hydrogen.

Preferred compounds I are those in which R(3) and R(3)′ represent a radical of the formula IV with R(4) equal to hydrogen, $(C_1-C_5)$-alkyl which is unsubstituted or substituted by OH or COOH, $(C_2-C_5)$-alkenyl, $(C_5-C_8)$-cycloalkyl, pyrrolyl, benzopyrrolyl, imidazolyl, phenyl, which is unsubstituted or substituted by $(C_1-C_4)$-alkyl, $(C_1-C_4)$-alkoxy, F, Cl, Br, $NO_2$ or CN.

Particularly preferred compounds I are those in which R(3) is the L-deoxyfucosyl group and R(3)′ is a radical SR(4) IV as defined above.

Very particularly preferred compounds I are those in which the macrodiolide ring is hydrogenated and in which R(3) is the L-deoxyfucosyl radical or hydrogen and R(3)′ is hydrogen.

The invention also relates to a process for the preparation of a compound I, according to which a) elaiophylin

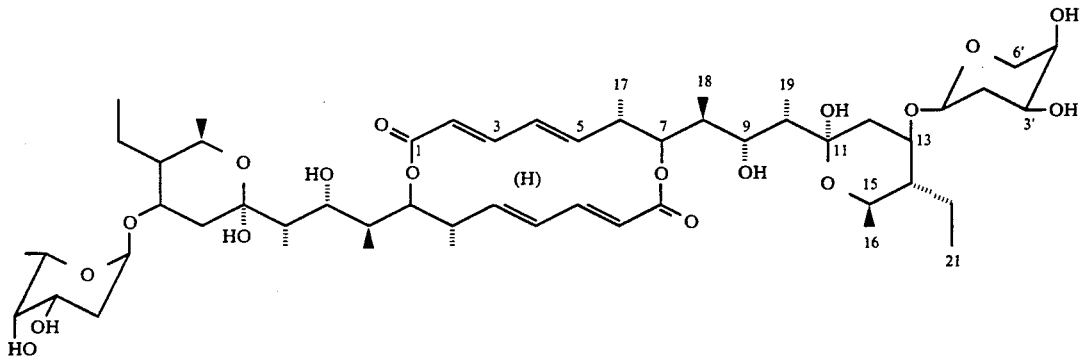

is reacted with a base in aqueous solvent at a pH of 8 to 11 to give a compound II

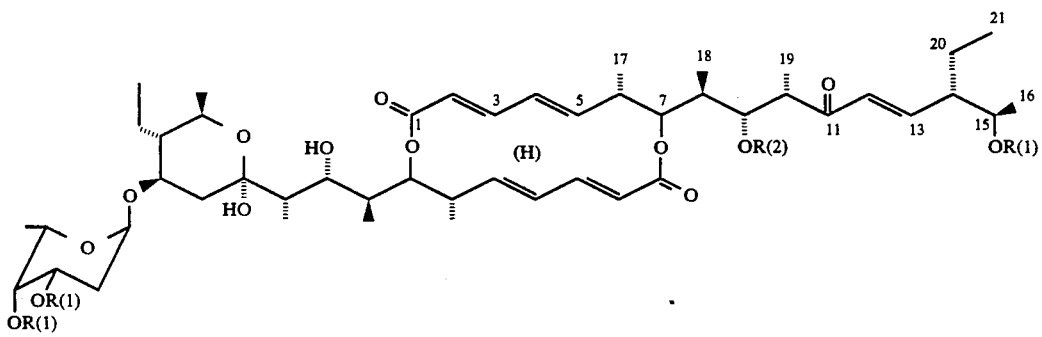

or III

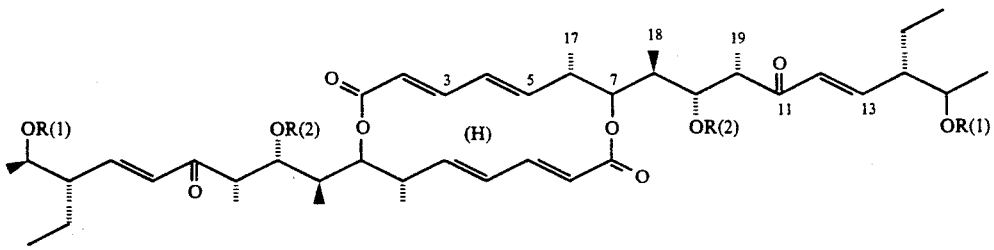

and the compound II or III which is obtained in this way and in which R(1)=R(2)=H is reacted with a thiol either of the formula IV

HSR(4)    IV in which R(4) is as defined in claim 1, to give a compound I, or the compound II or III which is obtained in this way and which has R(1)=R(2)=H is completely hydrogenated, in which case compounds I with R(3)=L-deoxyfucose and R(3) equals hydrogen are obtained from compounds II, and compounds I with R(3)=R(3)'=hydrogen are obtained from compounds III with R(1)=R(2)=hydrogen; or b) a compound II

HSR(4)

in which R(4) is as defined in claim 1, in which case the compound I with R(3)=L-deoxyfucose and R(3)'=SR(4) IV is obtained from compound II; and the compound I with R(3)=R(3)'=SR(4) from compound III; or c) a compound II or III in which the C—C double bonds in the macrodiolide ring can also be hydrogenated and which has R(1)=R(2)=H is completely hydrogenated, in which case compounds I with R(3)=L-deoxyfucose and R(3)' equals hydrogen are obtained from compounds II, and compounds I with R(3)=R(3)'=hydrogen are obtained from compounds

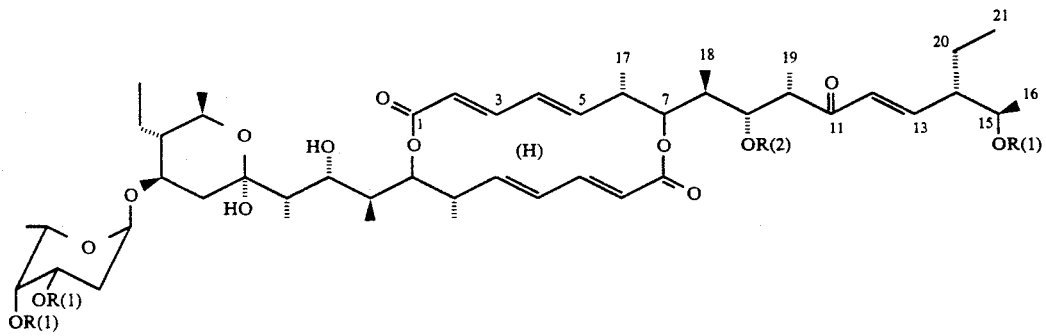

or III

III with R(1)=R(2)=hydrogen.

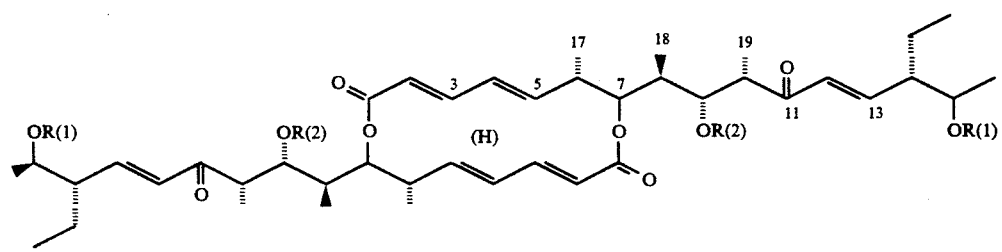

in which R(1)=R(2)=H is reacted with a thiol of the formula

The invention additionally relates to compounds III

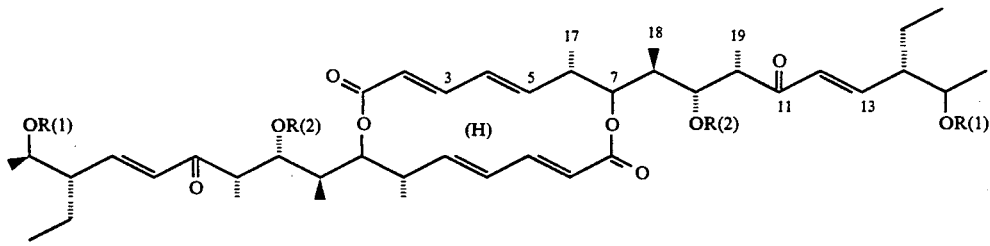

in which the following substituents have the following meaning

R(1) and R(2), identical or different, hydrogen, a radical of the formula V or V'

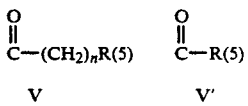

with n=1-3 and R(5) equal to $(C_1-C_5)$-alkyl, $(C_2-C_{15})$-alkenyl, $(C_2-C_{15})$-alkynyl, $(C_3-C_9)$-cycloalkyl, phenyl, naphthyl, furyl, thienyl, unsubstituted or substituted by F, Cl, Br, I, $NO_2$, CN, OH, COOH, $(C_1-C_4)$-alkyl or $(C_1-C_4)$-alkoxy, and in the case where R(1) equals H, R(2) also equals H, a radical of the formula VI

 VI with R(6) equal to $(C_1-C_{10})$-alkyl, phenyl, tolyl, and in the case where R(1) equals H, R(2) also equals H.

The invention is also directed at compounds II with R(6) equal to $(C_1-C_{10})$-alkyl, phenyl, tolyl, and in the case where R(1) equals H, R(2) also equals H.

Also preferred are intermediate compounds II and III in which R(1) and R(2) are hydrogen or, independently of one another, represent a radical of the formula V in which R(5) has the meaning $(C_1-C_5)$-alkyl, $(C_5-C_6)$-cycloalkyl or phenyl, and in the case where R(1) is hydrogen, R(2) is also hydrogen. Likewise preferred are compounds II and III in which R(1) represents a radical of the formula VI with $R(6)=(C_1-C_5)$-alkyl, phenyl or tolyl. All these compounds possess as antibacterial activity against bacteria pathogenic for humans, as well as antiviral activity.

The compounds I, II and III are obtained by various processes.

a. Elaiophylin is reacted in a solvent mixture with a base which has a pH of 8 to 11, in which case the L-deoxyfucose is eliminated by $\beta$-elimination to give compound II (R(1), R(2)=H) and compound III (R(1), R(2)=H).

b. If compound II or III with R(1)=R(2)=hydrogen is reacted with a thiol of the formula HSR(4) as defined

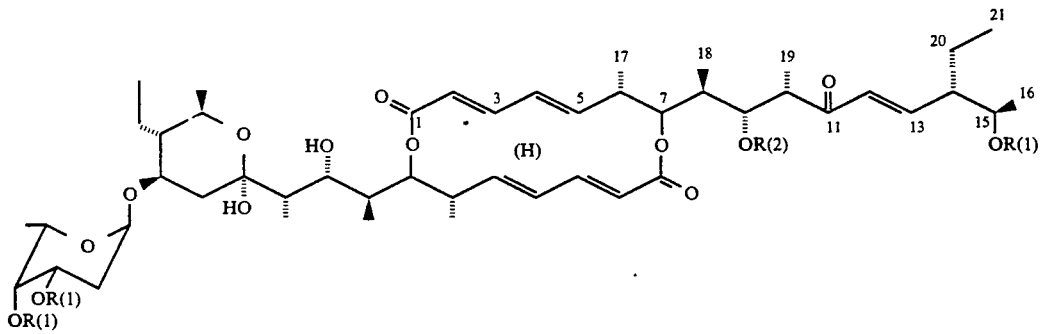

in which the following substituents have the following meaning

R(1) and R(2), identical or different, hydrogen, a radical of the formula V or V'

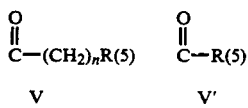

with n=1-3 and R(5) equal to $(C_1-C_5)$-alkyl, $(C_2-C_{15})$-alkenyl, $(C_2-C_{15})$-alkynyl, $(C_3-C_9)$-cycloalkyl, aryl, heteroaryl, unsubstituted or substituted by halogen, $NO_2$, CN, OH, COOH, $(C_1-C_4)$-alkyl or $(C_1-C_4)$-alkoxy, and in the case where R(1) equals H, R(2) also equals H, a radical of the formula VI

 VI above, the corresponding compounds I are obtained by nucleophilic addition onto the enone system. Thus, II gives the compound I with R(3)=L-deoxyfucose and R(3)'=IV, and III gives the compound I with R(3)=R(3)'=IV.

c. If compound II or III with R(1)=R(2)=H is completely hydrogenated with hydrogen, the compound I with R(3)=L-deoxyfucose and R(3)'=hydrogen is obtained from II, and the compound I with R(3)=R(3)'=hydrogen is obtained from compound III (octahydrodideoxyelaiophylidene).

d. If compound II or III with R(1)=R(2)=hydrogen or R(1)=V or V' as defined above, or R(1)=VI as defined above, and R(2)=hydrogen is reacted with a compound of the formula VII or VII'

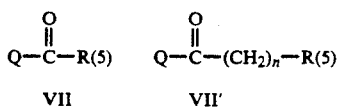

VII

VII' in which n and R(5) have the meaning specified under V and V', and Q denotes chloride, bromide, imidazolide or acid anhydride, a compound with R(1)=V or V' and R(2)=hydrogen or compounds with R(1), R(2)=V or V' are obtained from compounds II or III with R(1)=R(2)=H, and compounds with R(1)=V or V' and R(2)=V or V', in which R(1) and R(2) are identical or different, are obtained from compounds II or III with R(1)=V and R(2)=hydrogen.

e. If a compound II or III with R(1)=R(2)=hydrogen or R(1)=V or V' as defined above, or R(1)=VI as defined above, and R(2)=hydrogen is reacted with a compound of the formula $ClSO_2R(6)$, compounds with R(1)=VI and R(2)=hydrogen or R(1)=R(2)=VI are obtained from compound II or III with R(1)=R(2)=hydrogen, or the derivatives with R(1)=V or V' and R(2)=VI are obtained from compounds II or III with R(1)=V or V', R(2)=hydrogen, as well as the derivatives with R(1)=VI and R(2), where R(1) and R(2) can be identical or different, are obtained from R(1)=VI and R(2)=hydrogen.

Processes a to e are described in more detail hereinafter. It is possible by variant a to eliminate the L-deoxyfucose side-chain from elaiophylin. This results in compounds II and III with R(1)=R(2)=hydrogen. The yield of II decreases and that of III increases with higher temperatures and longer reaction times.

The best procedure is to suspend elaiophylin in a mixture of water, alcohol and an inert organic solvent. Suitable alcohols are methanol, ethanol and isopropanol, and suitable inert solvents are chloroform, ethyl acetate, THF, methylene chloride.

The mixture of water, ethanol and ethyl acetate is preferred. The reaction temperatures are between 20° C. and the boiling point of the reaction mixture. The reaction is preferably carried out under reflux. The reaction times amount to 0.5 to 180 hours, preferably 1 to 24 hours. The completion of the reaction is determined by thin-layer chromatography. Bases which are used are alkali metal and alkaline earth metal hydroxides and carbonates and bicarbonates. The pH of the reaction solution should be between 7 and 14, preferably between 8 and 11. Sodium bicarbonate and potassium bicarbonate at a pH of 8 to 11 are very particularly preferred. The pH can be controlled with HCl or $H_2SO_4$ or via an appropriate buffer.

The elaiophylin required as starting substance can be prepared by known preparation processes. That of German Patent Application P 3721722.4 is a suitable example. This results in elaiophylin as a product of fermentation of cultures of the strains DSM 4137 and DSM 3816.

In process b, compound II or III with R(1)=R(2)=hydrogen is dissolved in a solvent such as alcohol or $CHCl_3$, $CH_2Cl_2$, THF, dioxane, and reacted with equimolar amounts or with an up to 50-fold excess of thiol of the formula $HSR_4$ in the presence of a base. Especially suitable bases are organic amines, preferably triethylamine, and alcohols which are used are especially methanol, ethanol or isopropanol. If salts $M^+-SR(4)$ are used directly, with $M^+$ equal to sodium+ or potassium+ for example, a suitable solvent is THF or dioxane. These salts are then prepared in THF or dioxane from HSR(4) by addition of the appropriate metal hydrides. The reaction temperatures are between 0° C. and the boiling point of the solvent. Temperatures between 50° C. and the boiling point are preferred. The reaction times are 0.1-180 hours, preferably 0.1 to 120 hours, depending on R(4).

The C—C double bonds of the macrodiolide ring as well as the enone double bond in II and III ($R_1=R_2=H$) can be hydrogenated by process variant c).

The best procedure for process variant c) is to react the elaiophylin derivative II $R_1/R_2=H$ or III $R_1/R_2=H$ which is to be hydrogenated and which is preferably dissolved in a solvent such as methanol, ethanol, isopropanol or ethyl acetate, or a mixture of these solvents or an aqueous mixture of these solvents, with hydrogen in the presence of a conventional hydrogenation catalyst by hydrogenation processes known from the literature. Examples of conventional hydrogenation catalysts are elements of group 8 such as platinum, palladium or else nickel, which are usually supported, for the purpose of increasing the reactive surface, on active carbon, silica or alumina supports, for example. If the reaction is carried out in an absolute primary alcohol as solvent, apart from a hydrogenation of the C=C double bonds there is also ketalization to give the $C_{11}/C_{11}'$-di-O-alkylene.

Depending on the catalyst used, the reaction can be carried out both without and with an excess pressure of hydrogen, for example up to 1 atmosphere. The reaction temperatures are between 0° C. and 40° C., preferably at room temperature. The reaction times depend on the batch size and the concentration of the compound to be reduced. Hydrogenation processes of this type are described, for example, in Organikum, Organisch Chemisches Grundpraktikum (Basic Techniques of Organic Chemistry), 15th edition, VEB Deutscher Verlag der Wissenschaften, Berlin, 1976, pages 359-371.

The hydroxyl groups in formula II and III can be esterified by process variant d). Since the reaction rate for esterification at the 3', 4' and 15 position—that is to say for the $R^1$ derivatives—is greater than the esterification at the 9 position, the possibility of providing for $R^1$ and $R^2$ both identical and different substituents opens up.

With higher temperatures and/or sufficiently long reaction times the OH group in the 9 position is also esterified. However, this also means that esterification in the 9 position is possible only after previous esterification of the OH groups in the 3', 4' and 15 position. Thus, for example, it is possible in this way for first the OH groups in the 3', 4' and 15 position to be esterified and, subsequently, where appropriate after isolation and purification of the product, for the OH group in the 9 position to be esterified in a second reaction corresponding to process variant a.

The best procedure for process variant b) is to react a compound of the formula II or III in which $R^1$, $R^2$ have the meanings specified above, in equimolar amounts or in an up to 50-fold excess, where appropriate in an inert aprotic solvent such as chloroform, methylene chloride, tetrahydrofuran (THF), ethyl acetate or dioxane, with a compound of the formula VII or VII' until the reaction is complete, where appropriate in the presence of a base, preferably pyridine.

The temperatures for this reaction are between −70° C. and +100° C., preferably when a solvent is used between the solidification point and the boiling point of the solvent, in particular between −70° C. and +40° C. The reaction times amount to 1 to 180 hours, preferably 1 to 48 hours, particularly preferably 1 to 8 hours. The completion of the reaction can be determined, for example, by thin-layer chromatography (TLC monitoring).

The starting compounds for process variant d), which are compounds of the formula VII and/or VII', can, where they cannot be bought, be prepared in a straightforward manner by processes known from the literature. For example, the acid chlorides are obtained by reacting the corresponding carboxylic acid with thionyl chloride, $PCl_3$ or $PCl_5$. Processes of this type are described, for example, in Gattermann/Wieland, "Die Praxis des Organischen Chemikers" (Practical Organic Chemistry), 43rd edition, Walter de Gruyter, Berlin, N.Y. 1982, pages 303 et seq.

The best procedure for process variant e) is to react an elaiophylin derivative II or III in equimolar amounts or in an up to 50-fold excess with sulfonyl halides of the formula $Y—SO_2R^6$.

This reaction can also be carried out with addition of base where appropriate. Examples of suitable bases are triethylamine, pyridine or lutidine. One variant of process e) comprises using a suitable, preferably inert solvent such as chloroform, methylene chloride, THF, ethyl acetate or dioxane. It is also possible in this case for the excess of the compounds listed above to be up to 50 times the amount.

The temperature for this reaction are between −70° C. and +100° C., preferably when a solvent is used between the solidification point and the boiling point of the solvent, in particular between −70° C. and −40° C. The reaction times amount to 1 to 180 hours, preferably 1 to 48 hours, particularly preferably 1 to 8 hours. The completion of the reaction can be determined, for example, by TLC monitoring.

The starting compounds for process variant e) can, where they cannot be bought, be prepared in a straightforward manner by processes known from the literature. For example, the sulfonyl halides of the formula $Y—SO_2R^6$ are obtained by radical reaction of alkanes with chlorine and $SO_2$ or by halogenation of aromatic compounds with halogenosulfonic acid $Y—SO_3H$.

The antiviral activity of the compounds I, II and III according to the invention was tested in cell cultures infected with test viruses. It emerged from this that the derivatives according to the invention have an exellent antiviral effect.

The compounds according to the invention are suitable, by reason of their pharmacological properties, for the treatment of bacterial diseases and viral diseases caused, for example, by HSV I, II (herpes simplex I or II virus) or else picorna- and retroviruses such as HIV (human immunodeficiency virus).

The invention therefore additionally relates to the use of the compounds of the formula I, II and III according to the invention for the treatment and prophylaxis of bacterial diseases or of herpes virus, picorna- and retroviral diseases.

The compounds can be used as pharmaceuticals either alone or mixed with physiologically tolerated auxiliaries or excipients. For this purpose they can be administered orally in doses of 0.01–5.0 mg/kg/day, preferably 0.01–1.0 mg/kg/day or parenterally subcutaneously in doses of 0.001–2.5 mg/kg/day, preferably 0.001–1.0 mg/kg/day, in particular 0.005–0.2 mg/kg/day. Topical use is particularly preferred, in which case the concentration of active substance in the ointments is 0.001–1%, preferably 0.01–0.1%. The dosage can also be increased in severe cases. However, lower doses also suffice in many cases. The statements relate to an adult weighing about 75 kg.

The invention additionally embraces the use of the compounds according to the invention for the preparation of pharmaceuticals which are used for the treatment and prophylaxis of the abovementioned diseases.

The invention further relates to pharmaceuticals which contain one or more compounds of the formula I, II and/or III according to the invention.

The pharmaceuticals are prepared by processes which are known per se and familiar to those skilled in the art. As pharmaceuticals, the pharmacologically active compounds (=active substance) according to the invention are used either as such or, preferably, in combination with suitable pharmaceutical auxiliaries or excipients in the form of tablets, coated tablets, capsules, suppositories, emulsions, suspensions or solutions, with the content of active substance being up to about 95%, preferably between 10 and 75%. On topical use, concentrations of active substance of 0.001–1%, preferably 0.01–0.1%, suffice.

Examples of suitable auxiliaries and excipients for the desired pharmaceutical formulation are, besides solvents, gel-formers, suppository bases, tablet auxiliaries and other active substance vehicles, also antioxidants, dispersing agents, emulsifiers, antifoam agents, flavorings, preservatives, solubilizers or colorants.

The active substances can be administered orally, parenterally (subcutaneously), topically or rectally, with topical application being preferred. The active compounds are mixed with the additives suitable for this purpose, such as excipients, stabilizers or inert diluents, and converted by the customary methods into suitable dosage forms such as tablets, coated tablets, hard gelatine capsules, aqueous, alcoholic or oily suspensions or aqueous or oily solutions, creams or ointments. Examples of inert excipients which can be used are gum arabic, magnesia, magnesium carbonate, potassium phosphate. This formulation can be carried out both as dry and as wet granules. Examples of suitable oily excipients or solvents are vegetable or animal oils such as sunflower oil or fish liver oil.

For subcutaneous or intravenous administration, the active compounds are converted, if desired with the substances suitable for this purpose, such as solubilizers, emulsifiers or other auxiliaries, into solution, suspension or emulsion. Examples of suitable solvents are physiologically saline or alcohols, for example ethanol, propanol, glycerol, as well as sugar solutions such as glucose or mannitol solutions, or else a mixture of the various solvents mentioned. The invention is explained in more detail hereinafter by means of examples.

EXAMPLES

Process a 12 mmol of elaiophylin are heated in 120 ml of water, 80 ml of ethanol and 70 ml of ethyl acetate with 25 g of $KHCO_3$ at 65° C. The mixture is then concentrated in vacuo, and the remaining aqueous phase is extracted with ethyl acetate (4×150 ml). Drying over sodium sulfate is followed by concentration in vacuo. The remaining residue is chromatographed on silica gel (elution with $CHCl_3/CH_3OH$ 40:1).

Process b 1 mmol of elaiophylin derivative is stirred in 30 ml of ethanol with 300 ml of ethanethiol and 300 ml of triethylamine at 60° C. for 1 hour. Addition of 50 ml of water is followed by extraction with ethyl acetate (3×50 ml). The ethyl acetate phase is washed with 30 ml of water (3×) and dried over sodium sulfate. Evaporation in vacuo is followed by chromatography of the residue on silica gel (ethyl acetate/hexane 1:4).

Process c 1 mmol of elaiophylin derivative 1 or 5 is dissolved in 30 ml of ethyl acetate, and 10% by weight of Pd/animal charcoal is added. Hydrogenation is carried out at room temperature while stirring in a closed hydrogenation apparatus maintaining a slight excess pressure of up to 0.2 bar of hydrogen. After 3 hours, the mixture is filtered and the solvent is removed. Chromatography on silica gel with ethyl acetate/hexane 1:3 to 3:1 yields the corresponding products.

Process d 1 mmol of elaiophylin derivative is dissolved in 20 ml of pyridine and stirred with 10 ml of acid anhydride at room temperature for 24 hours. Hydrolysis with 60 ml of water is followed by extraction with ethyl acetate (3×30 ml). The organic phase is washed with 10 ml of 1N HCl and 20 ml of water and dried over sodium sulfate. Evaporation to dryness in vacuo in a rotary evaporator is followed by chromatography on silica gel (elution $CHCl_3/CH_3OH$ from 30:1 to 10:1).

Process e 1 mmol of elaiophylin derivative is dissolved in 20 ml of pyridine and stirred with 10 mmol of methanesulfonyl chloride at room temperature for one hour. Hydrolysis with 60 ml of water is followed by working up as in process d.

Physicochemical data on the compounds prepared

| No. | $MNa^+$ | melting point | $^{13}C$ in $CDCl_3$ |
|---|---|---|---|
| 1 | 898 | 876,3 | 202,6, 168,4, 168,0, 148,2, 145,4, 145,3, 145,1, 144,9, 131,6, 131,4, 122,2, 122,1, 100,29, 94,2 |
| 2 | 1067 | 1045,6 | |
| 3 | 1359 | 1337,6 | |
| 4 | 1901 | 1379,5 | |
| 5 | 751 | 728.9 | 202,6, 168,0, 148,3, 145,2, 245,0, 131,6, 131,4, 122,3, 76,8, 72,2, 68,9 |
| 6 | 919 | 897,1 | 200,4, 170,3, 170,1, 167,4, 146,0, 145,8, 144,4, 132,4, 131,7, 122,0, 75,2, 74,4, |
| 7 | 959 | 937,2 | 202,23, 168,9, 167,9, 165,9, 150,0, 149, 149,3, 76,8, 72,8, 72,0 |
| 8 | 907 | 885,1 | 202,0, 168,0, 145,4, 145,1, 143,8, 132,8, 131,4, 122,2 80,9, 76,9, 71,9 |
| 9 | 891* | 852,2 | 168,5, 195,4, 195,0, 131,5, 122,0, 99,2, 76,9, 70,1, 68,3 |
| 10 | 907* | 884,2 | 168,5, 145,3, 145,0, 131,5, 122,0, 99,1, 76,9, 70,8, 68,3, 62,4, |
| 11 | 763 | 741,06 | Schmp. 152–153° C. |
| 12 | 908 | 886.2 | |

*$MK^+$

| Examples No. | Formula | $R_1$ | $R_2$ | $R_3$, | $R_3$ | Synth. from | Reagent | Reaction time in h | Process | Yield |
|---|---|---|---|---|---|---|---|---|---|---|
| 1 | II | H | H | — | — | ELA | $KHCO_3$ | 6 | a | 44% |
| 2 | II | Ac | Ac | — | — | 1 | $Ac_2O$ | 24 | d | 85% |
| 3 | II | Bz | H | — | — | 1 | $Bz_2O$ | 24 | d | 72% |
| 4 | II | Bz | Ac | — | — | 3 | $Ac_2O$ | 24 | d | 70% |
| 5 | III | H | H | — | — | ELA | $KHCO_3$ | 14 | a | 75% |
| 6 | III | Ac | Ac | — | — | 5 | $Ac_2O$ | 24 | d | 85% |
| 7 | III | Bz | H | — | — | 5 | $Bz_2O$ | 24 | d | 78% |
| 8 | III | $CH_3SO_2$ | H | — | — | 5 | $CH_3SO_2Cl$ | 11 | e | 92% |
| 9 | I | — | — | $SCH_2CH_3$ | $SCH_2CH_3$ | 5 | $CH_3CH_2SH$ | 1 | b | 88% |
| 10 | I | — | — | $SCH_2CH_2OH$ | $SCH_2CH_2OH$ | 5 | $HOCH_2CH_2SH$ | 1 | b | 86% |
| 11 | I hydrogenated | — | — | H | H | 5 | $Pd/H_2$ | 3 | c | 92% |
| 12 | I hydrogenated | — | — | H | L-Deoxy-fucose | 5 | Pd/12 | 3 | c | 94% |

Ac = Acetyl
Bz = Benzoyl

Antiviral activity

Antiviral activity in cell cultures

The test substances were dissolved in cell culture medium (Dulbecco's MEM) and introduced in a series of geometrical dilutions with a factor of 3 into 100 μl of cell culture medium in standard microtiter plates. Subsequently added were 100 μl of a suspension of HeLa or Vero cells in medium containing 5% fetal calf serum in a cell density of $2 \times 10^5$ cells/ml. The mixtures were infected with 50 μl of the particular test virus in a suspension which was adjusted such that the cells showed a cytopathogenic effect within 72 h. Evaluation was carried out by microscopic inspection of the cell lawn and photometric measurement of the uptake of neutral red (Finther staining test). The MIC was taken to be the concentration of the product (μg/ml) at which about 50% of the cells survived the infection (MIC=-minimum inhibitory concentration).

Table 1 shows the effect (MIC data in μg/ml) of various compounds according to the invention against the following viruses:

Herpes simplex virus I, herpes simplex virus II

TABLE 1

| Compound No. | Herpes I | Herpes II |
|---|---|---|
| 1 | 4.94 | 4.94 |
| 9 | 44.4 | 14.8 |
| 10 | 4.94 | 1.65 |

We claim:
1. A compound III

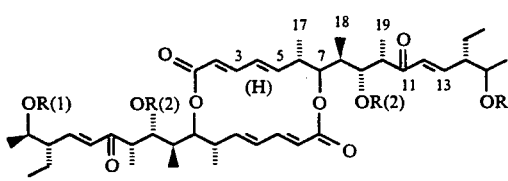

wherein
R(1) and R(2) denote, identically or differently, hydrogen, a radical of the formula V or V'

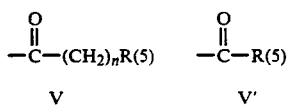

wherein n equals 1-3 and R(5) is equal to $(C_1-C_5)$-alkyl, $(C_2-C_{15})$-alkenyl, $(C_2-C_{15})$-alkynyl, $(C_3-C_9)$-cycloalkyl, phenyl, naphthyl, furyl, thienyl, unsubstituted or substituted by halogen, $NO_2$, CH, OH, COOH, $(C_1-C_4)$-alkyl or $(C_1-C_4)$-alkoxy, and in the case where R(1) equals H, and R(2) also equals H, a radical of the formula VI

SO₂R(6)   VI wherein R(6) is equal to $(C_1-C_{10})$-alkyl, phenyl, or tolyl.

2. A process for the preparation of a compound I of the following formula:

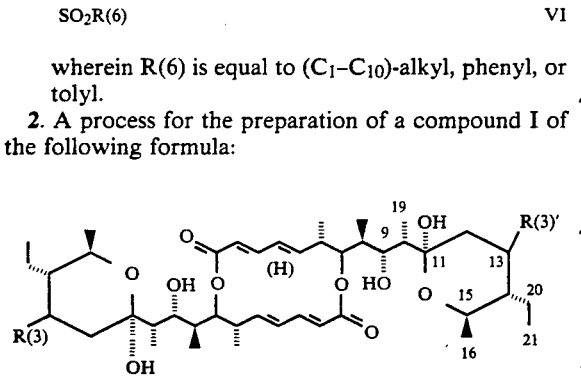

where the C—C double bonds in the macrodiolide ring of said compound I can also be hydrogenated, wherein, in said formula:
a) R(3) and R(3)', being identical or different, are a radical of the formula IV

—SR(4)

where R(4) is hydrogen, $(C_1-C_{10})$-alkyl which is unsubstituted or substituted by OH or COOH, $(C_2-C_{10})$-alkenyl, $(C_3-C_8)$-cycloalkyl, pyrrolyl, benzopyrrolyl, imidazolyl, benzimidazolyl, triazolyl, tetrazolyl, phenyl, with the aromatic or heteroaryl radicals being unsubstituted or substituted once or twice by $(C_1-C_4)$-alkyl, $(C_1-C_4)$-alkoxy, $(C_1-C_4)$-alkylcarbonyl, carboxyl, F, Cl, Br, I, $NO_2$, or CN;

b) R(3) is L-deoxyfucose and R(3)' is as defined under a); or
c) if the C—C double bonds in the macrodiolide ring are hydrogenated:
R(3) and R(3)' are hydrogen or
R(3) is L-deoxyfucose and R(3)' is hydrogen;
said process comprising the steps wherein:
a) elaiophylin

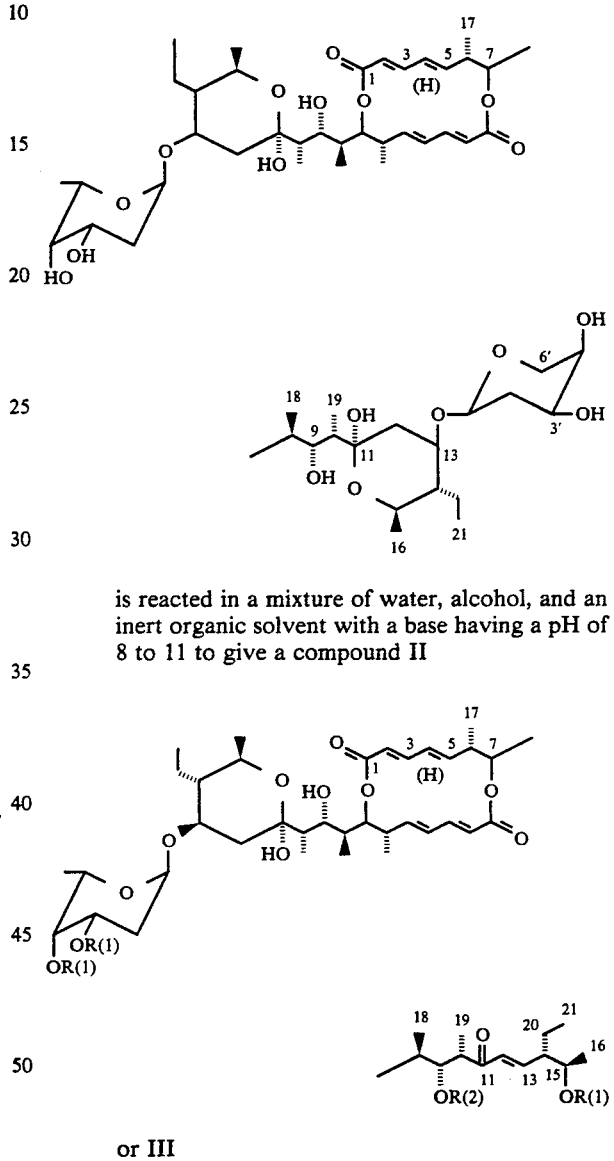

is reacted in a mixture of water, alcohol, and an inert organic solvent with a base having a pH of 8 to 11 to give a compound II and the compound II or III, which is obtained in this way and in which R(1)=R(2)=H, is reacted with a thiol ether of the formula IV

HSR(4)

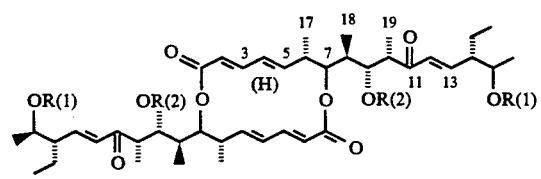

in which R(4) is as defined above, to give a compound I, or in the case in which compound II or III is obtained in this way and in which R(1)=R(2)=H is completely hydrogenated with hydrogen, a compound I wherein R(3)=L-deoxyfucose and R(3)'=hydrogen is obtained from compound II, and a compound I wherein R(3)=R(3)'=hydrogen is obtained from compound III; or said process comprises the steps wherein:

b) a compound II

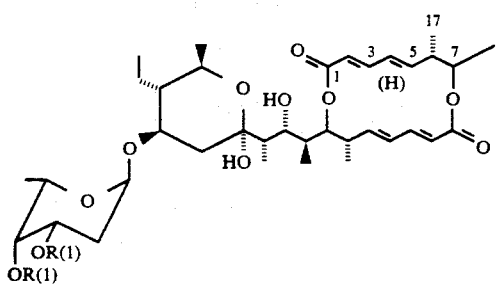

or III

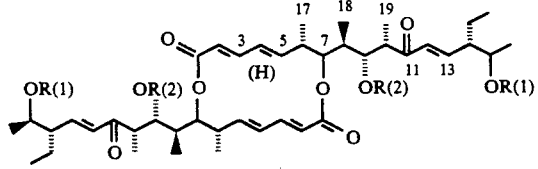

in which R(1)=R(2)=H is reacted with a thiol of the formula

HSR(4)

in which R(4) is as defined above, in which case a compound I wherein R(3)=L-deoxyfucose and R(3)'=SR(4) is obtained from compound II; and a compound I wherein R(3)=R(3)'=SR(4) is obtained from compound III; or said process comprises the steps wherein:

c) a compound II or III in which the C—C double bonds in the macrodiolide ring can also be hydrogenated and in which R(1)=R(2)=H is completely hydrogenated, in which case a compound I with R(3)=L-deoxyfucose and R(3)'=hydrogen is obtained from compound II, and a compound I with R(3)=R(3)'=hydrogen is obtained from compound III.

3. A process for the preparation of a compound I according to claim 2 wherein said alcohol is selected from the group consisting of methanol, ethanol and isopropanol.

4. A process for the preparation of a compound I according to claim 2 wherein said inert organic solvent is selected from the group consisting of chloroform, ethyl acetate, tetrahydrofuran, methylene chloride and dioxane.

5. A process for the preparation of a compound I according to claim 2 wherein said base is selected from the group consisting of alkali metal and alkaline earth metal hydroxides, carbonates and bicarbonates.

6. A process for the preparation of a compound I according to claim 2 wherein the elaiophylin is reacted in a mixture of water, ethanol, ethyl acetate and sodium bicarbonate or potassium bicarbonate, said mixture having a pH of 8 to 11.

* * * * *